(12) United States Patent
Xia et al.

(10) Patent No.: US 11,905,554 B2
(45) Date of Patent: Feb. 20, 2024

(54) SIMPLE, COST-EFFECTIVE AND AMPLIFICATION-BASED WHOLE GENOME SEQUENCING APPROACH

(71) Applicants: HAINAN UNIVERSITY, Haikou (CN); Zhiqiang Xia, Haikou (CN)

(72) Inventors: Zhiqiang Xia, Haikou (CN); Meiling Zou, Haikou (CN); Wenquan Wang, Haikou (CN)

(73) Assignee: HAINAN UNIVERSITY

( * ) Notice: Subject to any disclaimer, the term of this patent is extended or adjusted under 35 U.S.C. 154(b) by 365 days.

(21) Appl. No.: 17/032,150

(22) Filed: Sep. 25, 2020

(65) Prior Publication Data

US 2022/0098639 A1    Mar. 31, 2022

(51) Int. Cl.
*C12Q 1/686* (2018.01)
*C12Q 1/6853* (2018.01)

(52) U.S. Cl.
CPC ........... *C12Q 1/686* (2013.01); *C12Q 1/6853* (2013.01)

(58) Field of Classification Search
None
See application file for complete search history.

(56) References Cited

FOREIGN PATENT DOCUMENTS

WO    WO-2020199127 A1 * 10/2020

* cited by examiner

*Primary Examiner* — Samuel C Woolwine
*Assistant Examiner* — Carolyn L Greene
(74) *Attorney, Agent, or Firm* — Jose Cherson Weissbrot

(57) ABSTRACT

A sequencing primer set comprising a universal upstream primer, a universal downstream primer and a downstream primer in rich of promoter; wherein the universal upstream primer has a sequence of: 5'-TBarcodeCAAAXXXXNNN-3'; the universal downstream primer has a sequence of: 5'-GACTGCGTACGZZZZNNN-3'(SEQ ID No. 9); the downstream primer in rich of promoter has a sequence of: 5'-GACTGCGTACYYNCTATA-3'(SEQ ID No. 7).

9 Claims, 4 Drawing Sheets

Specification includes a Sequence Listing.

SEQUENCE LISTING

```
<160> NUMBER OF SEQ ID NOS: 9

<210> SEQ ID NO 1
<211> LENGTH: 17
<212> TYPE: DNA
<213> ORGANISM: Artificial Sequence
<220> FEATURE:
<223> OTHER INFORMATION: universal upstream primer
<220> FEATURE:
<221> NAME/KEY: misc_feature
<222> LOCATION: (15)..(17)
<223> OTHER INFORMATION: n is a, c, g, or t

<400> SEQUENCE: 1
tcttatcaaa ccggnnn                                                  17

<210> SEQ ID NO 2
<211> LENGTH: 17
<212> TYPE: DNA
<213> ORGANISM: Artificial Sequence
<220> FEATURE:
<223> OTHER INFORMATION: universal upstream primer
<220> FEATURE:
<221> NAME/KEY: misc_feature
<222> LOCATION: (15)..(17)
<223> OTHER INFORMATION: n is a, c, g, or t

<400> SEQUENCE: 2
tgtagacaaa ccggnnn                                                  17
```

-continued

```
<210> SEQ ID NO 3
<211> LENGTH: 17
<212> TYPE: DNA
<213> ORGANISM: Artificial Sequence
<220> FEATURE:
<223> OTHER INFORMATION: universal upstream primer
<220> FEATURE:
<221> NAME/KEY: misc_feature
<222> LOCATION: (15)..(17)
<223> OTHER INFORMATION: n is a, c, g, or t

<400> SEQUENCE: 3
tcctcgcaaa ccggnnn                                                  17

<210> SEQ ID NO 4
<211> LENGTH: 17
<212> TYPE: DNA
<213> ORGANISM: Artificial Sequence
<220> FEATURE:
<223> OTHER INFORMATION: universal upstream primer
<220> FEATURE:
<221> NAME/KEY: misc_feature
<222> LOCATION: (15)..(17)
<223> OTHER INFORMATION: n is a, c, g, or t

<400> SEQUENCE: 4
tgaactcaaa ccggnnn                                                  17

<210> SEQ ID NO 5
<211> LENGTH: 17
<212> TYPE: DNA
<213> ORGANISM: Artificial Sequence
<220> FEATURE:
<223> OTHER INFORMATION: universal upstream primer
<220> FEATURE:
<221> NAME/KEY: misc_feature
<222> LOCATION: (15)..(17)
<223> OTHER INFORMATION: n is a, c, g, or t

<400> SEQUENCE: 5
tttactcaaa ccggnnn                                                  17

<210> SEQ ID NO 6
<211> LENGTH: 18
<212> TYPE: DNA
<213> ORGANISM: Artificial Sequence
<220> FEATURE:
<223> OTHER INFORMATION: universal downstream primer
<220> FEATURE:
<221> NAME/KEY: misc_feature
<222> LOCATION: (16)..(18)
<223> OTHER INFORMATION: n is a, c, g, or t

<400> SEQUENCE: 6
gactgcgtac gaattnnn                                                 18

<210> SEQ ID NO 7
<211> LENGTH: 18
<212> TYPE: DNA
<213> ORGANISM: Artificial Sequence
<220> FEATURE:
<223> OTHER INFORMATION: downstream primer in rich of  promoter
<220> FEATURE:
<221> NAME/KEY: misc_feature
<222> LOCATION: (13)..(13)
<223> OTHER INFORMATION: n is a, c, g, or t

<400> SEQUENCE: 7
gactgcgtac yynctata                                                 18
```

```
<210> SEQ ID NO 8
<211> LENGTH: 18
<212> TYPE: DNA
<213> ORGANISM: Artificial Sequence
<220> FEATURE:
<223> OTHER INFORMATION: universal downstream primer
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (16)..(18)
<223> OTHER INFORMATION: n is a, c, g, or t

<400> SEQUENCE: 8
gactgcgtac gtatannn                                              18

<210> SEQ ID NO 9
<211> LENGTH: 18
<212> TYPE: DNA
<213> ORGANISM: Artificial Sequence
<220> FEATURE:
<223> OTHER INFORMATION: universal downstream primer
<220> FEATURE:
<221> NAME/KEY: misc_feature
<222> LOCATION: (12)..(18)
<223> OTHER INFORMATION: n is a, c, g, or t

<400> SEQUENCE: 9
gactgcgtac gnnnnnnn                                              18
```

SIMPLE, COST-EFFECTIVE AND AMPLIFICATION-BASED WHOLE GENOME SEQUENCING APPROACH

REFERENCE TO SEQUENCE LISTING SUBMITTED VIA EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:
File Name: 143_28_Sequence_Listing replacement.txt
Date of Creation: May 3, 2023
Size (bytes): 2817 bytes

TECHNICAL FIELD

The present application relates to the field of gene sequencing, in particular to the design of a sequencing primer, and a simple, cost-effective and amplification-based whole genome sequencing approach.

BACKGROUND

Genotyping is a series of genetic analysis, including molecular marker discovery and a genotyping using high-throughput sequencing technology, one of the most powerful applications is plant breeding, which opens up new possibilities for plant breeding and plant genetics research. It provides a cost-effective platform for whole genome scanning and multiple sequencing. Simplified sequencing technology is a new application of high-throughput sequencing, which is used to mine the single nucleotide polymorphism (SNP) in species populations and perform the genetic analysis. Bioinformatics tools are needed to analyze and parse simplified sequencing datasets. Because of low-cost technology and an excellent MAS tool, the simplified sequencing has been successfully applied to whole genome associated analysis and research, molecular marker mining, genetic linkage map, genome genetic selection and population genomic diversity research in large-scale plant molecular breeding strategies.

Simplified genome sequencing is a kind of sequencing technology developed on the basis of the second generation sequencing, which uses enzyme digestion technology, sequence capture chip technology or other experimental means to reduce the complexity of species genome, specific regions of the genome are sequenced, and then part of the genome sequence structure information is reflected. At present, simplified genomic sequencing has been developed, such as polymorphic sequencing with reduced complexity, restriction site related DNA sequencing, genotyping sequencing and so on.

A simple, fast and cost-effective system has been used for sequencing in non-model organisms. In particular, the most widely used is the sequencing technology of restriction site related DNA, which uses the restriction enzyme to cut the genome, produce a certain size fragment, construct the sequencing library, and carry out high-throughput sequencing for the restriction site markers produced after the restriction enzyme digestion. Because restriction site markers are small fragments of DNA tags near specific restriction sites in the whole genome range, they represent the sequence characteristics of the whole genome, thousands of single nucleotide polymorphism markers can be obtained in most organisms by sequencing of restriction site markers.

The sequencing-based genotyping is a new application of high-throughput sequencing to discover and analysis of the single nucleotide polymorphisms for crop improvement. The low cost of simplified sequencing makes it an attractive method for mapping and reproducing populations completely through the high-density single nucleotide polymorphism markers. The continuous improvement of sequencing and base calling software will enable high-throughput sequencing technology to provide higher sequencing flux for each run, thus achieving deeper multiplicity, so as to obtain the fixed average sequencing depth of each sample. With the increasing quantity and quality of sequence information generated by each run, the plex of each sample is higher and the cost is lower, simplified sequencing has become a cost competitive alternative to other whole genome genotyping platforms. Plant breeders will be able to sequence large crop genomes and build high-density genetic linkage maps from breeding populations. Future applications of simplified sequencing in crop improvement may allow plant breeders to label new germplasm or species without first developing any previous molecular tools. Because sequence based genotyping can be used for whole genome research, simplified sequencing will become one of the main components of plant genetics and breeding.

Identification of the high-density single nucleotide polymorphism markers by simplified sequencing to build genetic spectrum is of great value for many applications in plant breeding.

Genotyping microarray is to design probes based on the flanking sequences of known single nucleotide polymorphism sites. After the probe is fixed onto the chip, the DNA of the sample to be tested is hybridized with the chip and the hybridization fluorescence signal is scanned to identify the genotype of probe sites (single nucleotide polymorphism sites). Representative brands are Illumina and aflymetrix.

The single nucleotide polymorphism microarray has become an important tool for crop genetic improvement. The era of molecular breeding has come, in order to solve the shortage of molecular marker detection methods, the traditional breeding cycle is long and the result is unpredictable, relying on breeders' experience and naked eye screening. The field can be moved to the laboratory for large-scale and accurate screening, and more than 95% of individual plants will be excluded, and the left small number of individual plants are planted in the field, which greatly reduces the field workload. The original breeding method has an average cycle of 8 to 10 years for one species, while the present method will be completed within three to five years.

At present, the chip has very high practical value in rapid identification of breeding materials, genome selection, germplasm resources analysis, variety improvement, QTL mapping, genetic analysis, variety authenticity identification and other aspects, and has great cost advantages. However, there are some difficulties in the application of chips, which limit the wide use of chips in crop genetic improvement. The main difficulties are as follows: (1) at present, the research and development cost of the chip is relatively high, and it needs to have sequenced genome as reference and known SNP markers; it can only detect the known SNP sites, and the number of obtained markers is small; it only detects existing SNP markers, but cannot find new SNP sites; the detection process has high dependency on instrument; and currently there are only a few breeding model species have corresponding chips;

(2) the cost of simplified sequencing is not low enough, because the establishment of the library is cumbersome and its efficiency is not high enough, it is difficult to widely use for the detection of large breeding samples; because of the need for enzyme digestion, the simplified sequencing requires high quality DNA, and it is impossible to use the directly separated DNA (direct PCR); the sequencing quantity of the samples was not uniform in the process of establishing library, which needs to be supplemented; there is no enrichment effect of gene region.

SUMMARY

The embodiments of the present application provide a sequencing primer set and a whole genome sequencing method based on PCR, which aims to solve the technical problems of slow speed on SNP sites, high requirements and complex operation of existing chip screening genome process.

The embodiment of the present application is realized as follows: according to the first embodiment, a sequencing primer set is provided, which includes a universal upstream primer, a universal downstream primer and a downstream primer in rich of promoter.

The sequence of the universal upstream primer includes: 5'-T[barcode]CAAAXXXXNN N-3'.

The sequence of the universal downstream primer includes: 5'-GACTGCGTACGZZZ ZNNN-3'(SEQ ID No. 9, wherein Z is represented by N in sequence listing).

The sequence of the downstream primer in rich of promoter includes: 5'-GACTGCGTACYYNCTATA-3'(SEQ ID No. 7).

In particular, the length of the "XXXX" is 4 bases, and each base is selected from the group consisting of A, T, C and G; the length of the "ZZZZ" is 4 bases, and each base is selected from the group consisting of A, T, C and G; the length of the "barcode" is 4-6 bases, and each base is selected from the group consisting of A, T, C and G; and the "N" is A, T, C or G. The "Y" is a base C or T.

According to the second embodiment, a PCR based whole genome sequencing method is provided, which includes the following steps:
  preparing the DNA of the sample to be tested;
  providing the above sequencing primer set, conducting the first PCR amplification on the DNA of the sample to be tested by using the universal upstream primer and the universal downstream primer to obtain the first amplification product, and conducting the second PCR amplification on the DNA of the sample to be tested by using the universal upstream primer and the downstream primer in rich of promoter to obtain the second amplification product;
  performing sequencing analysis on the first amplification product and the second amplification product separately.

The sequencing primer set provided by the invention includes universal upstream primer, universal downstream primer and downstream primer in rich of promoter with specific sequences, wherein the universal upstream primer and universal downstream primer respectively include four bases: "XXXX" and "ZZZZ" (the bases are all selected from the group consisting of A, T, C and G), these eight bases are the core base regions of the universal primers, which can be varied according to the changes of the genome of the sample to be tested. According to different bases, it can amplify different sequence fragments on different genomes. The primer scheme can be optimized according to the sequence of genome, and the genome size and sample size can be adjusted. On the other hand, by mimicking the base sequence of the upstream region of eukaryotes, the primers with the characteristics of promoter region are designed, that is, the downstream primers in rich of promoter, in this way, the sequences near the promoter could be effectively amplified by universal upstream primers and the downstream primers for enriching promoter. Such a primer set used for whole genome amplification and sequencing, not only has a good enrichment effect, but also makes the library construction and sequencing more concise and accurate, and reduces the cost of sequencing.

Meanwhile, a whole genome sequencing method based on PCR is provided by the invention, which can amplify the DNA of the sample to be tested by using the sequencing primer set to obtain the PCR product of the sample to be tested, and then sequencing analysis can be conducted. The above whole genome sequencing method based on PCR has the characteristics of "discovery" and "detection" of the single nucleotide polymorphism (SNP) sites, can detect and screen the whole genome at the same time of discovering new markers, therefore, it does not need to build a chip in the early stage, and does not need to mark the known single nucleotide polymorphism (SNP) sites, on the other hand, when this method is used to sequence the whole genome, the quality of sample DNA is not required to be high, and the establishment of the library is more simple and convenient, and it has high coverage, gene region enrichment effect and short sequencing time, so it can be widely used in genome sequencing of different samples.

DETAILED DESCRIPTION OF THE EMBODIMENTS

Figure 1:
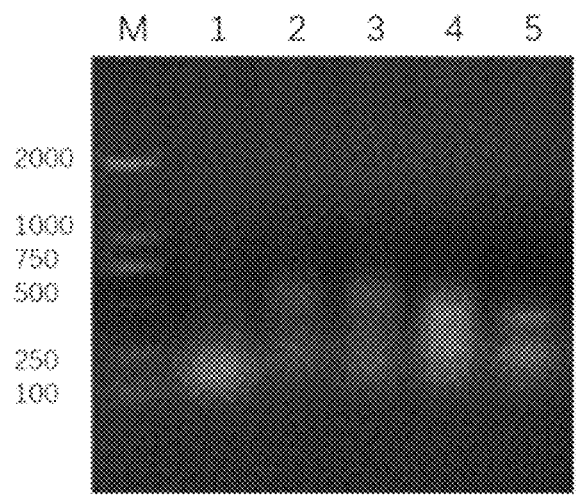
FIG. 1 is the agarose electrophoresis analysis result of PCR products of five samples with universal primers provided in Example 1 of the present application.

In order to make the purpose, technical solution and advantages of the present application more clear, the present application will be further described in detail with reference to the accompanying drawings and examples. It should be understood that the examples described herein are intended to explain the invention only and are not intended to limit the invention.

The embodiments of the present application provide a sequencing primer set, the sequencing primer set includes a universal upstream primer, a universal downstream primer and a downstream primer in rich of promoter;

The sequence of the universal upstream primer includes: 5'-T[barcode]CAAAXXXXNNN-3'(SEQ ID No. 9;

The sequence of the universal downstream primer includes: 5'-GACTGCGTACGZZZZNNN-3'(SEQ ID No. 7);

The sequence of the downstream primer in rich of promoter includes: 5'-GACTGCGTACY YNCTATA-3';

wherein the length of the "XXXX" is 4 bases, and the base is selected from the group consisting of A, T, C and G; the length of the "ZZZZ" is 4 bases, and the base is selected from the group consisting of A, T, C and G. The length of "barcode" is 5 bases, and the base is selected from the group consisting of A, T, C and G; the "N" is a base in any one of A, T, C and G, and the "Y" is the base C or T.

In particular, the length of the "XXXX" is 4 bases, and the base is selected from the group consisting of A, T, C and G. The length of the "ZZZZ" is 4 bases, and the base is selected from the group consisting of A, T, C and G. These eight bases are the core base regions of the universal primers, which can be varied according to the changes of the genome of the samples to be tested, accordingly, according to the different bases, the eight bases can be used to amplify different sequences in different genomes. Specifically, the "barcode" is designed on the universal upstream primer, and the length of "barcode" is 5 bases and each can be selected from the group consisting of A, T, C and G or their combination. Preferably, the "barcode" has 5 bases, and can be any random combination of base A, T, C and G, a total of 384 "barcode" can be selected. In the preferred examples of the present application, any number of "barcode" sequences can be added according to different samples to further distinguish the samples. The added "barcode" varies based on the different genomes of the samples to be tested, and the purpose of adding "barcode" is to distinguish each different sample, that is to distinguish each DNA sequence.

In particular, the downstream primer in rich of promoter is: 5'-GACTGCGTACYYNCTATA-3'(SEQ ID No. 7). The principle of designing a downstream primer in rich of promoter is to design a primer with promoter region characteristics by simulating the upstream region base sequence of eukaryotes, i.e. downstream primer in rich of promoter, so that the primer can effectively amplify the sequence near the promoter region, and further achieve the purpose of gene region enrichment, which is conducive to the follow-up experiments.

Preferably, in the universal upstream primer, the universal downstream primer and the downstream primer in rich of promoter, the "N" is any one of base A, T, C and G, and the "Y" is base C or T. By further designing "N" and "Y" bases onto the primers, on the one hand, it can improve the coverage of primers and make the primers amplify the whole genomic DNA to a greater extent; on the other hand, the design method with mixed bases can further improve the binding ability of primers onto the samples to be tested, so as to achieve the purpose of gene de-enrichment. The "N" is a random base, and several random bases are designed at the end of the universal primer, which can eliminate the bias effect of PCR enrichment, and so as to restore the original genome, which has great advantages in the analysis of copy number. Preferably, the "N" can be designed as 3-8 groups with any number of base positions, it can simplify the genome to a greater extent, and can be used in complex genome or large genome, and can be adjusted freely to reduce the cost (larger sample, less SNP).

In a preferred embodiment of the present application, taking cassava (*Manihot esculenta* Crantz) as the detection object, in the sequencing primer set, the sequence of the universal upstream primer is 5'-T[barcode]CAAACCGG-NNN-3', and the sequence of the universal downstream primer is 5'-GACTGCGTACGAATTNNN-3'(SEQ ID No. 6); or, the sequence of the universal upstream primer is: 5'-T [barcode] CAAACGCGNNN-3', and the sequence of the universal downstream primer is 5'-GACTGCGTACGTA-TANNN-3'(SEQ ID No. 8).

By analyzing the gene sequences with high frequency in cassava gene, the core primer base "XXXX" of universal upstream primer is determined as "CCGG" or "CGCG", and the core primer base "ZZZZ" of universal downstream primer is determined as "AATT=" or "ATAT". Selecting the high frequency bases in cassava gene as the core primer bases can further improve the coverage of amplification and have good enrichment effect.

In another preferred embodiment of the present application, cassava is taken as the detection object, and the "barcode" is selected from the group consisting of CTTAT, GTAGA, CCTCG, GAACT and TTACT. According to the difference of cassava samples, a "barcode" with a length of 5 bases was designed onto the universal upstream primers, and in order to distinguish each DNA sequence from others, and ensure more uniform amplification, the coverage rate in the whole genome is higher and more comprehensive.

Therefore, compared with the prior art, the sequencing primer set provided by the present application includes universal upstream primer, universal downstream primer and downstream primer for enrichment promoter with specific sequences, wherein the universal upstream primer and universal downstream primer each includes four bases: "XXXX" and "ZZZZ" (the bases are all selected from the group consisting of A, T, C and G), these eight bases are the core base regions of the universal primers, which can vary according to the changes of the genome of the sample to be tested. According to the different bases, it can amplify different sequence fragments on different genomes. The primer scheme can be optimized according to the sequence of genome, and the size of genome and sample size can be adjusted optionally. By simulating the upstream region base sequences of eukaryotes, primers with promoter region characteristics are designed, that is, the downstream primers in rich of promoter, in this way, the sequences near the promoter can be effectively amplified by universal upstream primers and downstream primers in rich of promoter. Such a primer set can be used for whole genome amplification and sequencing, it not only has a good enrichment effect, but also makes the library construction and sequencing more concise and accurate, and reduces the cost of sequencing.

Accordingly, one embodiment of the present application also provides a PCR based whole genome sequencing method, which comprises the following steps:

S01. Preparing the DNA of the sample to be tested;

S02. Providing the sequencing primer set, using the universal upstream primer and universal downstream primer to carry out the first PCR amplification on the DNA of the sample to be tested to obtain the first amplification product, and using the universal upstream primer and the downstream primer in rich of promoter to carry out the second PCR amplification on the DNA of the sample to be tested to obtain the second amplification product;

S03. Sequencing and analyzing the first amplification product and the second amplification product respectively.

In particular, in the above step S01, DNA of the sample to be tested is prepared. In the preferred example of the invention, the method for preparing the DNA of the sample to be tested is selected from any one of the whole genome DNA extraction method, PCR kit amplification method and lysing tissue method with lysate.

Preferably, the method for whole genomic DNA extraction mainly includes cetyltrimethylammonium bromide (CTAB) method, this method mainly uses cationic detergents to precipitate nucleic acid and acidic polysaccharide from low ionic strength solution, while in high ion concentration solution, cetyltrimethylammonium bromide forms complex with protein and polysaccharide, but does not precipitate nucleic acid. After removing impurities such as proteins, polysaccharides and phenols by organic solvent extraction, ethanol is added for precipitation, to separate the nucleic acid, and obtain the whole genome DNA; or SDS (sodium dodecyl benzene sulfonate) is used to lyse cells to separate chromosomes and denaturate proteins, at the same time, SDS combines with proteins and the polysaccharides to form complex and release the nucleic acid. Secondly, PCR kit amplification method can be directly used for direct preparation; or lysing tissue method with lysate to extract the whole genome DNA. Since the follow-up test does not require high quality of DNA, the direct PCR method described in the embodiments of the present application can quickly enrich and obtain the whole genome DNA of the sample, meanwhile the requirement for DNA quality is not high, and the method is simple and fast, which greatly shortens the preparation time of library and improves the test efficiency.

In particular, in the above S02 step, the sequencing primer set is provided, the first PCR amplification product is obtained by using the universal upstream primer and the universal downstream primer to perform the first PCR amplification on the DNA of the sample to be tested, and the second PCR amplification product is obtained by using the universal upstream primer and the downstream primer in rich of promoter to perform the second PCR amplification on the DNA of the sample to be tested.

Preferably, the steps of the first PCR amplification include:

First, binding the universal upstream primer and the universal downstream primer with the DNA of the sample to be tested for binding amplification, and then the enrichment amplification for enriching target region is carried out.

In particular, the general PCR system (20 μL system) is as follows:

| DNA sample (20 ng) | 1.0 μL |
| 2 × NEB Taq Master Mix | 10 μL |
| 5 μM Primer universal upstream primer (corresponding to 5 samples) | 0.6 μL |
| 5 μM Primer universal downstream primer | 0.6 μL |
| ddH$_2$O | 7.8 μL; |

The binding amplification includes: 94° C. for 5 min, 5 cycles of the following reaction procedures: 94° C. for 1 min; 35° C. for 1 min, 72° C. for 1.5 min; and The enrichment amplification includes 35 cycles of the following reaction procedures: 94° C. for 1 min; 50-58° C. for 1 min; 72° C. for 1.5 min.

72° C., 7 min.

Preferably, the second PCR amplification step includes:

First, the universal upstream primer and the downstream primer in rich of promoter are bound with the DNA of the sample to be tested for binding amplification, and then the enrichment amplification for enriching target region is carried out.

In particular, the PCR system (20 μL system) for enriching Promoter region is as follows:

| DNA sample (20 ng) | 1.0 μL |
| 2 × NEB Taq Master Mix | 10 μL |
| 5 μM Primer universal upstream primer (corresponding to 5 samples) | 0.6 μL |
| 5 μM Primer universal downstream primer | 0.6 μL |
| ddH$_2$O | 7.8 μL; |

The binding amplification includes: 94° C. for 5 min, 5 cycles of the following reaction procedures: 94° C. for 1 min; 35° C. for 1 min, 72° C. for 1.5 min; and The enrichment amplification includes 35 cycles of the following reaction procedures: 94° C. for 1 min; 50-58° C. for 1 min; 72° C. for 1.5 min.

72° C., 7 min.

In particular, the main purpose of binding amplification is to bind the above primers with the sample DNA. The number of PCR reaction cycles for binding amplification is 5, with this number, all the primers could bind onto the DNA strand of the sample. According to the bases of "XXXX", "ZZZZ", "N" and "Y" designed on the primers, the annealing temperature is 35° C., which is low, and by using this pre-amplification step, setting a lower annealing temperature, the "XXXX", "N" and "Y" designed on the primers can be accurately and quickly combined with the sample DNA, and the primers are positioned on the sample DNA, which is conducive to the subsequent enrichment.

Preferably, the main purpose for enriching amplification is to enrich the gene and produce enrichment effect, which is convenient for subsequent detection. In the preferred embodiment of the invention, the number of PCR reaction cycles for enrichment amplification is 35, and the number of cycles has been increased to 35, which is mainly to amplify a large number of sample DNA and increase the number of enriched fragments of sample DNA. Moreover, based on the length of each primer, the annealing temperature is set to be 50-58° C., a suitable temperature can increase the amplification rate, and increase the enrichment amount.

In particular, in the above step S03, the first amplification product and the second amplification product are sequenced and analyzed separately. In one preferred embodiment of the present application, agarose gel electrophoresis is employed to detect the first amplification product and the second amplification product, respectively, so as to ensure that the product can be obtained by PCR amplification. Preferably, the first amplification product is quantized to the concentration of 180-200 ng/μL, and the second amplification product is quantized to the concentration of 180-200 ng/μL, so as to keep the concentration of each PCR product consistent. If the concentration of PCR products is too low, then the amount of obtained PCR amplified products is less, which is easy to be interfered by impurities in the following test; if the concentration is too high, the amount of PCR amplified product is too high, and the analysis is not clear due to the high concentration in the following test, and the sequencing result is not clear.

It is preferred that the first amplification product is adjusted to the same concentration and then all samples are mixed to obtain a first mixture, and the second amplification product is adjusted to the same concentration and then all samples are mixed to obtain a second mixture. Preferably, the mixing method is any one of suction mixing or centrifugal mixing. In the specific examples of the present application, the single sample is quantitated separately, and then the samples are mixed together and sequenced, which can overcome the problem of the uniformity of the output data amount of the common simplified sequencing.

Preferably, the first mixture and the second mixture are respectively subjected to the second generation sequencing for library construction and the sequencing results are analyzed. Preferably, the illumina sequencing is usually required for the second generation sequencing analysis for library construction. In the preferred examples of the present application, the obtained sequencing results can be analyzed by using the different [barcode]s of different designed primers to distinguish samples for analysis, so as to not only detect, but also mine population mutation sites.

Compared with the prior art, the present application provides a whole genome sequencing method based on PCR, which can amplify the DNA of the sample to be tested by using the sequencing primer set to obtain the PCR product of the sample to be tested, and then conduct sequencing analysis. The above whole genome sequencing method based on PCR takes into account the characteristics of "discovery" and "detection" of the single nucleotide polymorphism (SNP) sites, can detect and screen the whole genome at the same time of finding new markers, accordingly, it does not need to build a chip in the early stage, and does not need to mark the known single nucleotide polymorphism (SNP) sites. On the other hand, using this method to perform whole genome sequencing, it does not require high quality on sample DNA, and the establishment of the library s more simple and convenient, and it has high coverage rate, gene region enrichment effect and short sequencing time, so it can be widely used in genome sequencing of different samples. The following description is carried out in combination with the specific examples.

EXAMPLE 1

A PCR based whole genome sequencing method was carried out to test different cassava varieties, It included the following steps:

Step 1: preparing the DNA of the sample to be tested;

Genomic DNA was extracted from different cassava varieties. Liquid nitrogen or refrigerator below −70° C. was required for long term storage of samples. The genomic DNA was extracted with DNeasy 96 Plant Kit (QIAGEN) kit.

The quality of the extracted genomic DNA was detected and quantified: agarose gel was labeled with lambda marker, and 1 μL of DNA was added to the 2 μL of 10× bromine phenol blue loading buffer, then mixed well and dripped into 0.8% agarose gel containing 0.5 μg/ml Goldview dye, 1×TAE buffer, 90 V electrophoresis for 40 min; gel imaging analysis system. (Tanon 4100) was employed to observe the DNA bands.

1-2 μL of DNA sample was taken to detect the genomic DNA via NANODROP 2000° C.

The DNA concentration was calculated based on the absorbance value at 260 nm, and the ratios of OD260/OD280 and OD260/OD230 were calculated to determine whether there were impurities such as polysaccharide, protein and RNA, so as to determine the purity of DNA.

Step 2: providing the sequencing primer set, using the universal upstream primer and universal downstream primer to carry out the first PCR amplification on the DNA of the sample to be tested to obtain the first amplification product, and using the universal upstream primer and the downstream primer in rich of promoter to carry out the second PCR amplification on the DNA of the sample to be tested to obtain the second amplification product.

In particular, five universal upstream primers were designed as follows:

SEQ ID NO. 1
(5'-TCTTATCAAACCGGNNNN-3'),

SEQ ID NO. 2
(5'-TGTAGACAAACCGGNNNN-3'),

SEQ ID NO. 3
(5'-TCCTCGCAAACCGGNNNN-3'),

SEQ ID NO. 4
(5'-TGAACTCAAACCGGNNNN-3') ,

SEQ ID NO. 5
(5'-TTTACTCAAACCGGNNNN-3'), wherein the [barcode] region has different sequences, the sequence of "XXXX" in the universal upstream primer was "GGCC", because "GGCC" was the sequence with high frequency in cassava, so "GGCC" was selected.

One universal downstream primer sequence was designed:

SEQ ID NO. 6
(5'-GACTGCGTACGAATTNNNN-3'), wherein "ZZZZ" sequence was "AATT", because "AATT" is a high frequency sequence in cassava, so "AATT" was selected.

One downstream primer in rich of promoter was designed:

SEQ ID NO. 7
(5'-GACTGCGTACYYNCTATA-3').

The first PCR amplification was performed on the DNA of the sample to be tested by using the universal upstream primer and the universal downstream primer, and the first PCR amplification steps included:

First, the universal upstream primer and the universal downstream primer were combined with the DNA of the sample to be tested for binding amplification, and then the enrichment amplification for enriching target region amplification was performed.

In particular, the general PCR system (20 μL system) was:

| | |
|---|---|
| DNA sample (20 ng) | 1.0 μL |
| 2 × NEB Taq Master Mix | 10 μL |
| 5 μM Primer universal upstream primer (corresponding to 5 samples) | 0.6 μL |
| 5 μM Primer universal downstream primer | 0.6 μL |
| ddH$_2$O | 7.8 μL; |

The binding amplification included: 94° C. for 5 min, and 5 cycles of the following reaction procedure: 94° C. for 1 min; 35° C. for 1 min; 72° C. for 1.5 min; and The enrichment amplification included: 35 cycles of the following reaction procedures: 94° C. for 1 min; 50-58° C. for 1 min; 72° C. for 1.5 min.

72° C. for 7 min

The universal upstream primer and the downstream primer in rich of promoter were used to carry out the second PCR amplification on the DNA of the sample to be tested, and the second PCR amplification comprises the following steps:

First, the universal upstream primer and the downstream primer in rich of promoter are used to combine onto the DNA of the sample to be tested to perform binding amplification, and then the enrichment amplification for enriching target region was carried out.

In particular, the PCR system for enriching promoter region (20 μL system) was as follows:

| | |
|---|---|
| DNA sample (20 ng) | 1.0 μL |
| 2 × NEB Taq Master Mix | 10 μL |
| 5 μM Primer universal upstream primer (corresponding to 5 samples) | 0.6 μL |
| 5 μM Primer universal downstream primer | 0.6 μL |
| ddH$_2$O | 7.8 μL; |

The binding amplification included: 94° C. for 5 min, and 5 cycles of the following reaction procedures: 94° C. for 1 min; 35° C. for 1 min; 72° C. for 1.5 min; and The enrichment amplification included 35 cycles of the following reaction procedures: 94° C. for 1 min; 50-58° C. for 1 min, 72° C. for 1.5 min.

72° C., 7 min.

Step 3: sequencing and analyzing the first amplification product and the second amplification product separately.

Figure 2:
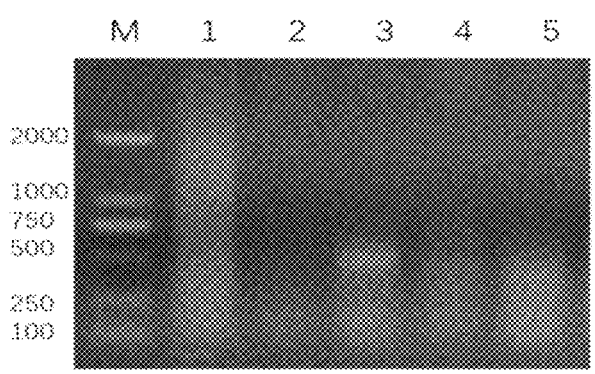
FIG. 2 is the agarose electrophoresis analysis result of PCR products of five samples with primers in rich of promoter region of five samples provided in example 1 of the present application.
Figure 3:
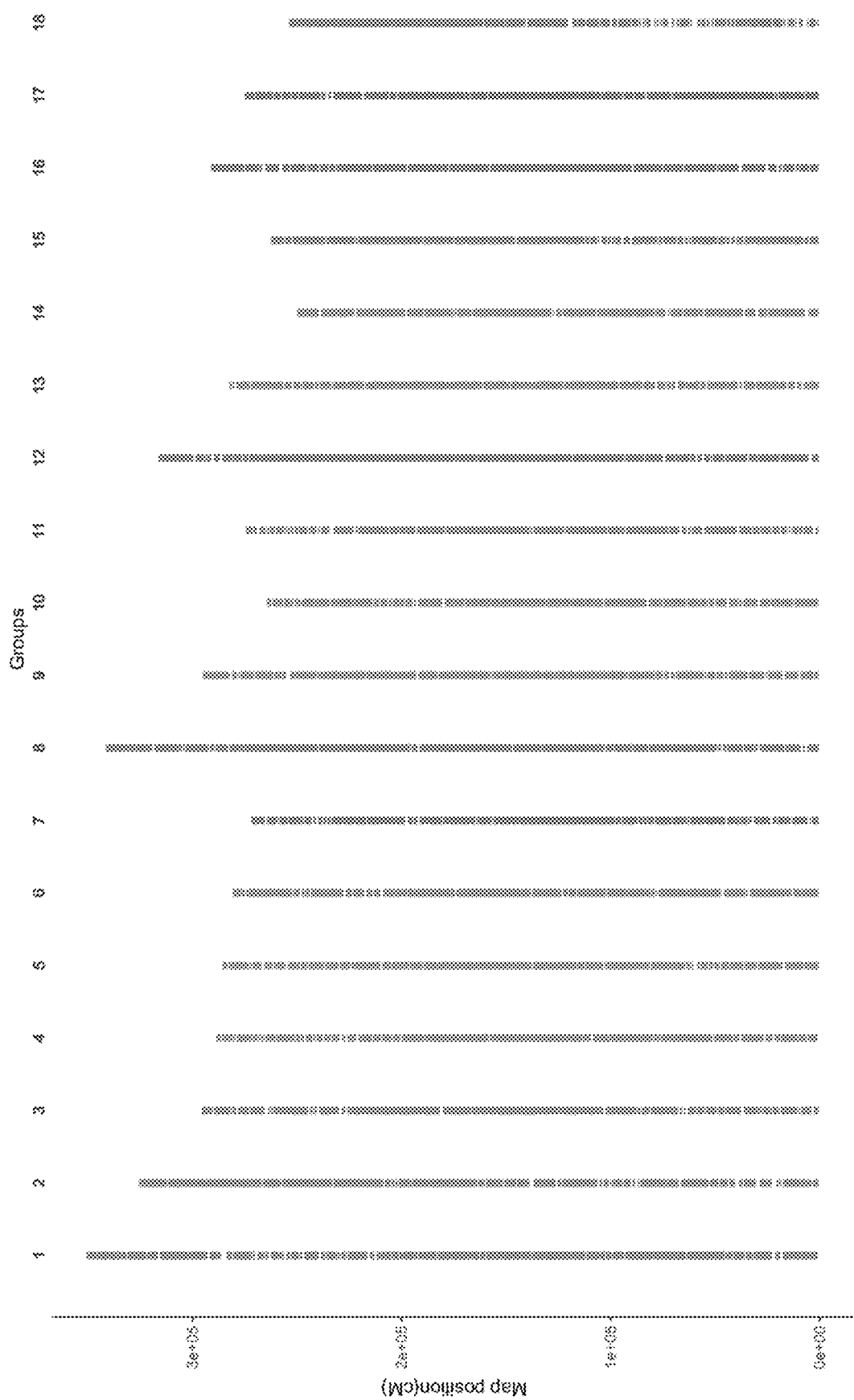
FIG. 3 is the analysis chart of genome coverage of sequencing reads obtained by universal primer method.
Figure 4:
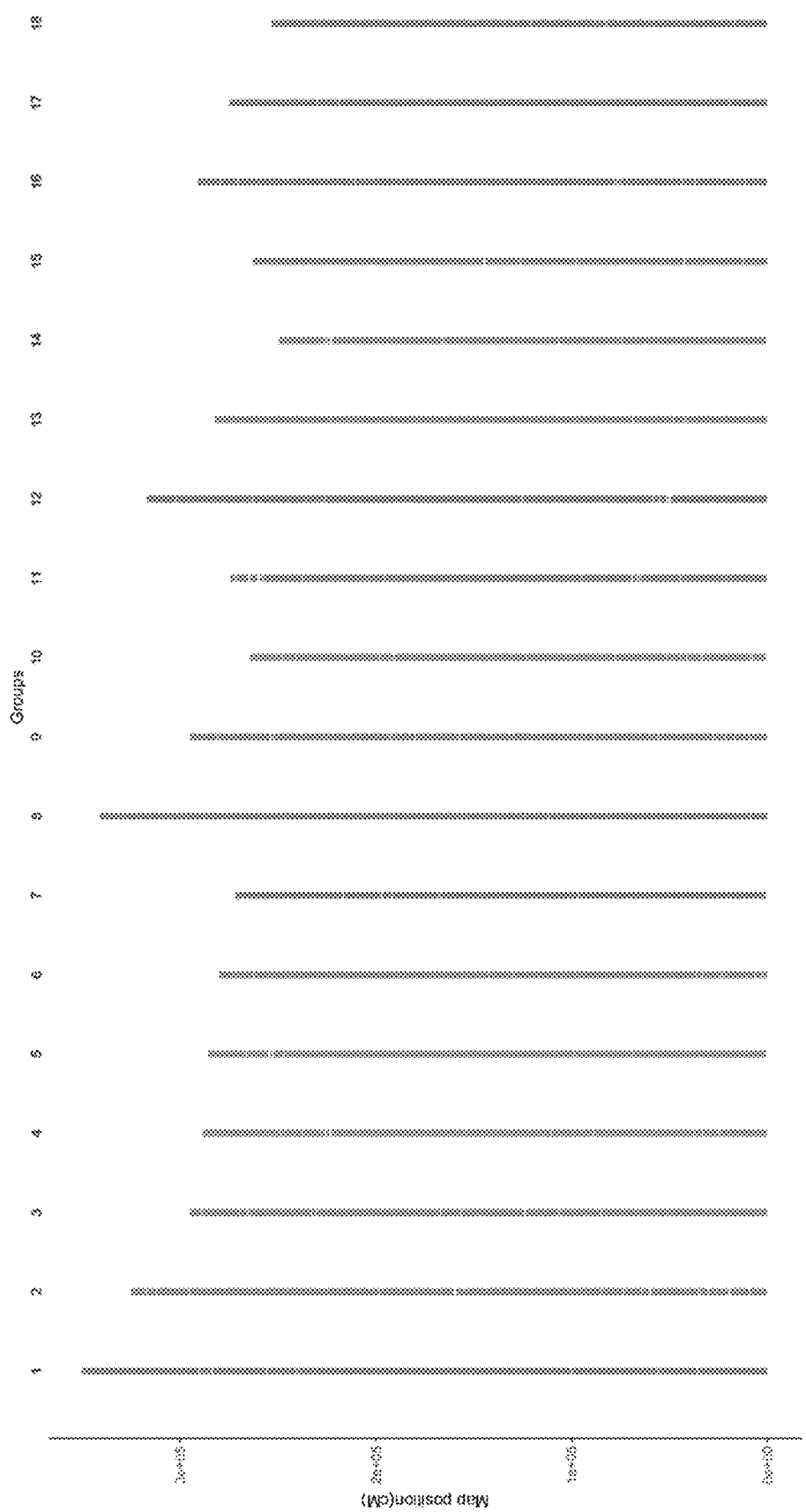
FIG. 4 is an analysis chart of genome coverage of sequencing reads obtained by method of primers in rich of promoter region.
Figure 5:
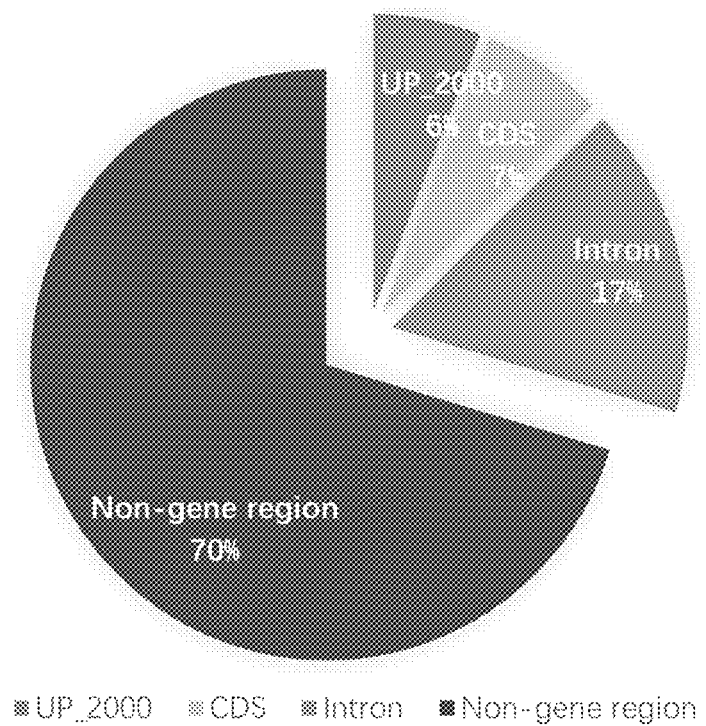
FIG. 5 shows the enrichment of PCR products in the gene region.

8 μL of the first amplification product and 8 μL of the second amplification product were detected with 2% agarose gel. The test results are shown in FIG. 1 and FIG. 2. FIG. 1 shows the detection results of the first amplification product from five samples, and FIG. 2 shows the detection result of the second amplification product from five samples. All PCR products should be homogenized and quantified to 100 ng/μL. 2 μL of the quantified first amplification product and 2 μL of the quantified second amplification product were taken from each sample and then mixed to obtain the first mixture and the second mixture. The 200 bp-700 bp fragment was recovered and purified. It was sent to a third-party sequencing company and sequenced with Hiseq2500, the sequencing length was 150 bp at both ends. The total data volume of original reads is 5 Gb. The sequencing results are shown in FIG. 3, FIG. 4 and FIG. 5. FIG. 3 shows the genomic coverage of sequencing reads obtained by universal primer method; FIG. 4 shows the genomic coverage of sequenced reads obtained by promoter enrichment region primer method; FIG. 5 shows the enrichment in gene region; it can be seen from FIG. 5 that 70% of PCR products are enriched in Non-gene region, 17% of PCR products are enriched in Intron region, and 7% of PCR products are enriched in CDS region, 6% of PCR products are enriched in UP_2000 region. Combining the above three graphs, it can be analyzed that the PCR method of the present application can be used for whole genome sequencing, and the coverage rate of the genome is very high, and the result has high reliability. At the same time, this method is more simple and convenient, with high coverage, gene region enrichment effect and short sequencing time, which can be widely used in genome sequencing of different samples.

The above-mentioned embodiments are only to explain the technical solutions of the present application, but not construed as a limitation on the present application; although the present application has been described in detail with reference to the above-mentioned embodiments, those persons of ordinary skill in the art should appreciate that the technical solutions described in the above embodiments can be modified, or substituted on some or total of the technical features of the same; and these modifications or substitutions do not deviate from the teaching and scope of the technical solutions of each embodiment of the present application, and they shall be included in the protection scope thereof.

What is claimed is:

1. A PCR based whole genome sequencing process comprising:
   preparing DNA of a sample to be tested;
   providing a sequencing primer set, conducting a first PCR amplification on the DNA of the sample to be tested by using the universal upstream primer and the universal downstream primer to obtain a first amplification product, and conducting a second PCR amplification on the DNA of the sample to be tested by using the universal upstream primer and the downstream primer with promoter to obtain a second amplification product;
   mixing the first amplification product and the second amplification product, and carrying out sequencing analysis;
   wherein the sequencing primer set comprising a universal upstream primer, a universal downstream primer and a downstream primer with promoter;
   wherein the universal upstream primer has a sequence of: 5'-TbarcodeCAAAXXXXNNN-3'; the universal downstream primer has a sequence of: 5'-GACTGCGTACGZZZZNNN-3' that is SEQ ID No. 9; the downstream primer with promoter has a sequence of 5'-GACTGCGTACYYNCTATA-3' that is SEQ ID No. 7;
   wherein the "XXXX" in the universal upstream primer has 4 bases, and each base of the "XXXX" is selected from the group consistong of A, T, C and G: the "ZZZZ" in the universal downstream primer has 4 bases, and each base of the "ZZZZ" is selected from the group consisting of A, T, C and G; the "barcode" in the universal upstream primer has 4-6 bases, and each base of the "barcode" is selected from the group consisting of A, T, C and G, and the "N" is selected from the group consisting of A, T, C and G, the "Y" is a base C or T.

2. The PCR based whole genome sequencing process of claim 1, wherein the first PCR amplification comprises:
   conducting a binding amplification by binding the universal upstream primer and the universal downstream primer to the DNA of the sample to be tested, and then performing an enrichment amplification of the target enrichment region.

3. The PCR based whole genome sequencing process of claim 2, wherein the binding amplification comprises: 94° C. for 5 minutes; and five cycles of a following procedure: 94° C. for 1 minute; 35° C. for 1 minute; 72° C. for 1.5 minutes.

4. The PCR based whole genome sequencing process of claim 2, wherein the enrichment amplification comprises 35 cycles of following procedure: 94° C. for 1 minute; 50 to 58° C. for 1 minute; 72° C. for 1.5 minutes; 72° C. for 7 minutes.

5. The PCR based whole genome sequencing process of claim 1, wherein the second PCR amplification comprises:
   conducting a binding amplification by binding the universal upstream primer and the downstream primer with promoter to the DNA of the sample to be tested, and then performing an enrichment amplification of the target region.

6. The PCR based whole genome sequencing process of claim 5, wherein the binding amplification comprises: 94° C. for 5 minutes; 5 cycles of following procedure: 94° C. for 1 minute; 35° C. for 1 minute; 72° C. for 1.5 minutes.

7. The PCR based whole genome sequencing process of claim 5, wherein the enrichment amplification comprises 35 cycles of following procedure: 94° C. for 1 minute; 50 to 58° C. for 1 minute; 72° C. for 1.5 minutes; 72° C. for 7 minutes.

8. The PCR based whole genome sequencing process of claim 1, wherein the method of preparing DNA of a sample to be tested comprises lysing the sample followed by performing whole genome DNA extraction or direct PCR on the lysate.

9. The PCR based whole genome sequencing process of claim 1, wherein before the sequencing analysis, the first amplification product is diluted to a concentration of 180-200 ng/μL, and the second amplification product is diluted to a concentration of 180-200 ng/μL.

\* \* \* \* \*